US011241281B2

(12) United States Patent
Govari

(10) Patent No.: US 11,241,281 B2
(45) Date of Patent: Feb. 8, 2022

(54) ESTIMATION OF ELECTRODE-TISSUE CONTACT USING OSCILLATOR AT COMMON GROUND OF ELECTROCARDIOGRAM (ECG) SYSTEM

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 362 days.

(21) Appl. No.: 16/102,144

(22) Filed: Aug. 13, 2018

(65) Prior Publication Data

US 2020/0046421 A1   Feb. 13, 2020

(51) Int. Cl.
*A61B 18/14* (2006.01)
*A61B 5/0538* (2021.01)
(Continued)

(52) U.S. Cl.
CPC ........ *A61B 18/1492* (2013.01); *A61B 5/0538* (2013.01); *A61B 5/063* (2013.01);
(Continued)

(58) Field of Classification Search
CPC ... A61B 18/1492; A61B 5/042; A61B 5/0538; A61B 5/063; A61B 18/1206;
(Continued)

(56) References Cited

U.S. PATENT DOCUMENTS 6,569,160 B1 * 5/2003 Goldin ............... A61B 18/1492
606/41
8,456,182 B2    6/2013 Bar-Tal et al.
(Continued)

FOREIGN PATENT DOCUMENTS

EP    335977 A1    10/1989
EP    1586281 A1   10/2005

OTHER PUBLICATIONS

Santos et al., Simultaneous Multi-Frequency Electrical Impedance Tomography, Aug. 16, 2016, Multidisciplinary Digital Publishing Institute (Year: 2016).*
(Continued)

*Primary Examiner* — Linda C Dvorak
*Assistant Examiner* — Nicholas S Borsch
(74) *Attorney, Agent, or Firm* — Dergosits & Noah LLP; Todd A. Noah

(57) ABSTRACT

A system includes signal acquisition circuitry, an oscillator circuit, and a processor. The signal acquisition circuitry is configured to receive from an intra-cardiac probe multiple intra-cardiac signals acquired by multiple electrodes of the probe, and to further receive a common ground signal for the multiple intra-cardiac signals. The signal acquisition circuitry is further configured to digitize the intra-cardiac signals relative to the common ground signal so as to produce multiple digital signals. The oscillator circuit is configured to generate an Alternating Current (AC) signal and to apply the AC signal to the common ground signal provided to the signal acquisition circuitry. The processor is configured to detect the AC signal in the multiple digital signals, and to assess, based on the detected AC signal, respective qualities of physical contact between the electrodes and cardiac tissue.

16 Claims, 2 Drawing Sheets

(51) Int. Cl.
*A61B 5/06* (2006.01)
*A61B 18/12* (2006.01)
*A61B 5/00* (2006.01)
*A61B 5/283* (2021.01)
*A61B 18/00* (2006.01)

(52) U.S. Cl.
CPC .......... *A61B 5/283* (2021.01); *A61B 18/1206* (2013.01); *A61B 5/062* (2013.01); *A61B 5/6852* (2013.01); *A61B 5/7203* (2013.01); *A61B 2018/00351* (2013.01); *A61B 2018/00577* (2013.01); *A61B 2018/00648* (2013.01); *A61B 2018/00666* (2013.01); *A61B 2018/00827* (2013.01); *A61B 2018/00875* (2013.01); *A61B 2560/0223* (2013.01)

(58) Field of Classification Search
CPC ........... A61B 2018/00827; A61B 2018/00648; A61B 2560/0223; A61B 2018/00351; A61B 5/6852; A61B 5/062; A61B 2018/00875; A61B 5/7203; A61B 2018/00666; A61B 2018/00577; A61B 5/721; A61B 5/6885; A61B 5/0424; A61B 5/0422; A61B 5/0402; A61B 5/0428; A61B 5/6869; A61B 5/6886; A61B 5/7221; A61B 2018/00369; A61B 2018/00404; A61B 5/287; A61B 5/283; A61B 5/282; A61B 5/28; A61B 2018/00636; A61B 2018/00642; A61B 2018/00654; A61B 2018/00845; A61B 5/7228; A61B 2018/00773; A61B 2018/00851; A61B 2018/008574
See application file for complete search history.

(56) References Cited

U.S. PATENT DOCUMENTS

| | | | |
|---|---|---|---|
| 9,585,593 | B2 * | 3/2017 | Fan ................. A61B 5/053 |
| 9,591,981 | B2 * | 3/2017 | Levin ................. A61B 5/296 |
| 2007/0073284 | A1 | 3/2007 | Sturm et al. |
| 2007/0171211 | A1 | 7/2007 | Perski et al. |
| 2010/0007413 | A1 | 1/2010 | Herleikson |
| 2012/0089140 | A1 | 4/2012 | Dunning et al. |
| 2012/0316497 | A1 | 12/2012 | Deutsch |
| 2016/0310077 | A1 | 10/2016 | Hunter et al. |
| 2016/0331262 | A1 * | 11/2016 | Kuck ................. A61B 5/055 |
| 2018/0078170 | A1 * | 3/2018 | Panescu ................. A61B 5/01 |

OTHER PUBLICATIONS

Analog Devices Proof of Date (Year: 2020).*
The Digital Domain, Apr. 21, 2010 (Year: 2010).*
Digital Domain Proof of Date (Year: 2020).*
Redmayne et al., Use a Single Input to Acquire Two Similar Signals Simultaneously and Other AC Techniques for the LTC1864, Apr. 10, 2018, Analog Devices (Year: 2018).*
Tait_Radio_Academy_ProofOfDate (Year: 2021).*
Basic Radio Awareness, Modulation and Radio Building Blocks, 2015, Tait Radio Academy (Year: 2015).*
Pending U.S. Appl. No. 15/991,291, filed May 29, 2018.
European Search Report for corresponding EPA No. 19191292.7 dated Nov. 13, 2019.

* cited by examiner

ESTIMATION OF ELECTRODE-TISSUE CONTACT USING OSCILLATOR AT COMMON GROUND OF ELECTROCARDIOGRAM (ECG) SYSTEM

FIELD OF THE INVENTION

The present invention relates generally to intrabody medical procedures and instruments, and particularly to cardiac electrocardiogram (ECG) sensing and ablation.

BACKGROUND OF THE INVENTION

Various known methods exist for recording electrophysiological signals. For example, U.S. Pat. No. 9,591,981 describes method for acquiring electrical signals from a living subject, including applying, via an electrode attached to the subject, a known calibration signal to the subject and measuring respective levels of output signals, generated at input electrodes attached to the subject, in response to the calibration signal. The method further includes deriving respective weighting factors for the input electrodes in response to the respective signal levels and applying the respective weighting factors to physiological signals acquired by the input electrodes, so as to generate respective corrected physiological signals.

As another example, U.S. Patent Application Publication 2016/0310077 describes a medical device and a sensor. In an embodiment, implantable sensor-modules containing contact sensors are placed on or within a kyphoplasty balloon in order to monitor contact between the balloon and a cancellous bone of a vertebral body.

U.S. Patent Application Publication 2007/0073284 describes a multiple RF return-pad contact detection system, which is adaptive to different physiological characteristics of patients without being susceptible to electrosurgical current interference (e.g., interference or measurement interaction between components of the detection system). The detection system can measure or sense the contact resistance or impedance between the patient and pairs of RF return-pads or return-electrodes where multiple pairs of RF return-pads are utilized due to the high current frequently needed during electrosurgery while eliminating or minimizing the risk of measurement interaction between the RF return-pad pairs. The system allows for the independent and simultaneous measurement of the pad contact impedance for each pair of RF return pads.

In another field, U.S. Patent Application Publication 2007/0171211 describes a detector for detecting touches of at least one object on a transparent sensor located over a display screen. The detector comprising a display screen, a patterned arrangement of conductors extending into said sensor situated over said display screen, and detection circuitry adapted to detect capacitive coupling of said at least one object with said at least one conductor. In an embodiment, an oscillating signal is provided by applying oscillations to the system or part thereof, in reference to the common ground.

SUMMARY OF THE INVENTION

An embodiment of the present invention provides a system including signal acquisition circuitry, an oscillator circuit, and a processor. The signal acquisition circuitry is configured to receive from an intra-cardiac probe multiple intra-cardiac signals acquired by multiple electrodes of the probe, and to further receive a common ground signal for the multiple intra-cardiac signals. The signal acquisition circuitry is further configured to digitize the intra-cardiac signals relative to the common ground signal so as to produce multiple digital signals. The oscillator circuit is configured to generate an Alternating Current (AC) signal and to apply the AC signal to the common ground signal provided to the signal acquisition circuitry. The processor is configured to detect the AC signal in the multiple digital signals, and to assess, based on the detected AC signal, respective qualities of physical contact between the electrodes and cardiac tissue.

In some embodiments, the oscillator circuit is configured to generate and apply the AC signal at two or more AC frequencies.

In some embodiments, the oscillator circuit is configured to generate and apply the two or more AC frequencies simultaneously.

In an embodiment, the oscillator circuit is configured to vary the AC signal over time between the two or more AC frequencies.

In another embodiment, the processor is configured to assess the qualities of physical contact by detecting, per intra-cardiac signal, whether the detected AC signal matches a frequency response of blood or of cardiac tissue.

In some embodiments, the processor is configured to assess the respective qualities of physical contact based on one or more AC signals uploaded from a memory.

In some embodiments, the processor is configured to assess the respective qualities of physical contact in real-time.

In an embodiment, the acquisition circuitry includes at least one Analog-to-Digital Converter (ADC), which is configured to simultaneously digitize at least one of the intra-cardiac signals and the corresponding AC signal.

There is additionally provided, in accordance with an embodiment of the present invention, a method, including receiving from an intra-cardiac probe multiple intra-cardiac signals acquired by multiple electrodes of the probe. A common ground signal for the multiple intra-cardiac signals is further received. The intra-cardiac signals are digitized relative to the common ground signal so as to produce multiple digital signals. An Alternating Current (AC) signal is generated and applied to the common ground signal provided to the signal acquisition circuitry. The AC signal is detected in the multiple digital signals, and, based on the detected AC signal, respective qualities of physical contact between the electrodes and cardiac tissue are assessed.

The present invention will be more fully understood from the following detailed description of the embodiments thereof, taken together with the drawings in which:

DETAILED DESCRIPTION OF EMBODIMENTS

Overview

Figure 1:
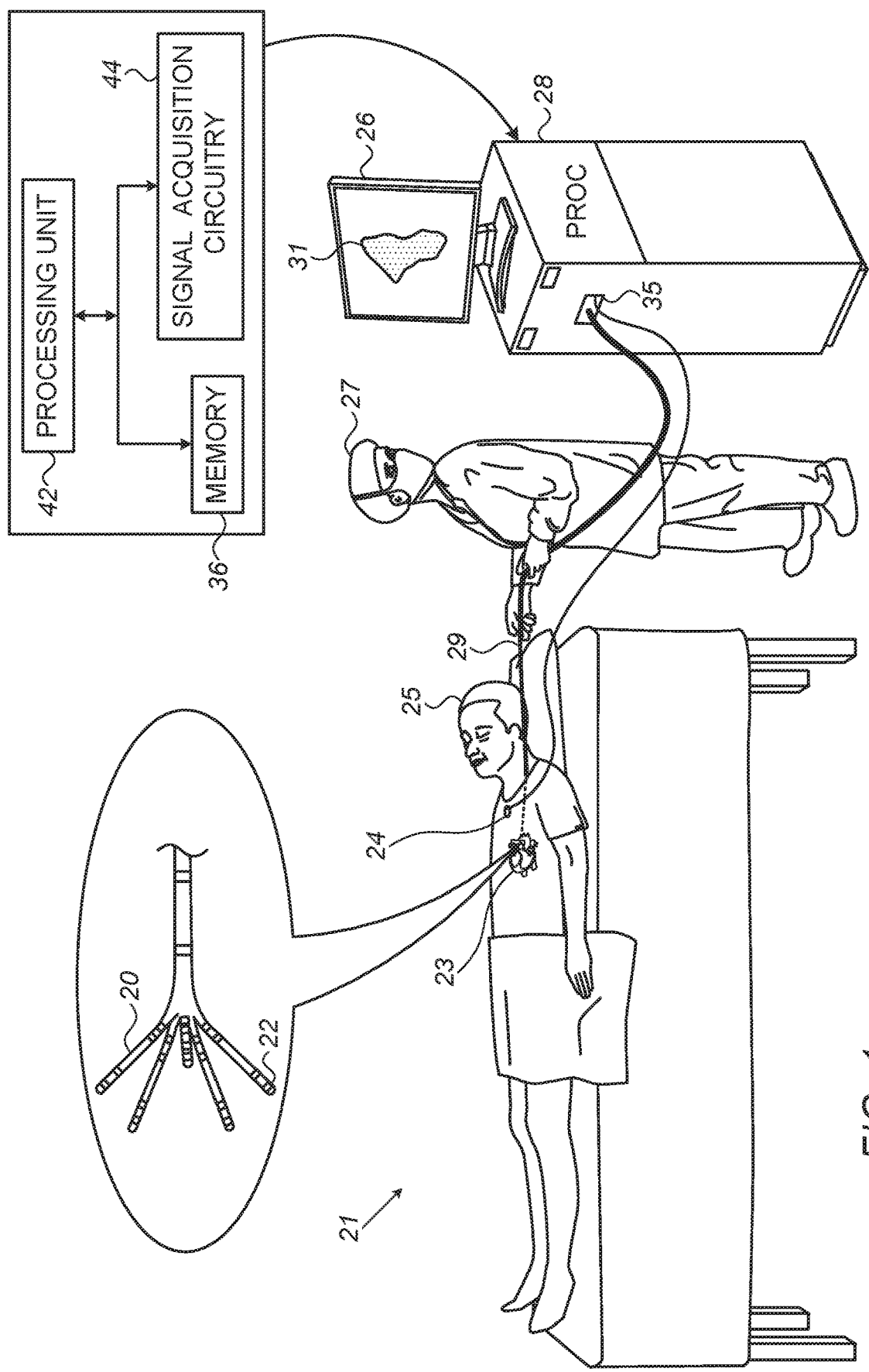
FIG. 1 is a schematic, pictorial illustration of a of an electro-anatomical mapping system, in accordance with an embodiment of the present invention.

Intra-cardiac probe based (e.g., catheter-based) cardiac diagnostic and therapeutic systems may measure multiple intra-cardiac signals, such as electrocardiograms (ECG), during an invasive procedure. Such systems may acquire the multiple intra-cardiac signals using electrodes (also named hereinafter "distal electrodes") that are fitted at the distal end of the probe.

In some cases, it may be required to verify that a distal electrode is in physical contact with cardiac tissue, such as the inner surface of a cardiac chamber, while the electrode acquires the intra-cardiac signals. Typically, in order to assess whether a distal electrode is in physical contact with tissue, another device, such as a contact force sensor, may be used. The introduction of an additional device may complicate the acquisition and analysis of the electrophysiological signals, for example, by causing electrical offsets and/or noises.

Embodiments of the present invention that are described hereinafter provide an intra-cardiac probe-based electro-anatomical measurement and analysis system and method that use signals that the distal electrodes already collect, for example, while measuring intra-cardiac ECG signals, in order to assess whether a distal electrode is in a physical contact with cardiac tissue while acquiring the intra-cardiac ECG signals.

In some embodiments, the disclosed probe-based electro-anatomical system includes signal acquisition circuitry, which is configured to receive from the intra-cardiac probe multiple intra-cardiac signals acquired by multiple electrodes of the probe, and to further receive a common ground signal for the multiple intra-cardiac signals. The signal acquisition circuitry digitizes the intra-cardiac signals relative to the common ground signal so as to produce multiple digital signals. The system further includes an oscillator circuit, which is configured to generate an Alternating Current (AC) signal and to apply the AC signal to the common ground signal that is provided to the signal acquisition circuitry (i.e., the oscillator circuit generates an AC floating common ground for the probe).

A processor in the system is configured to detect the AC signal in the multiple digital signals, and to assess, based on the detected AC signal, respective qualities of physical contact between the electrodes and cardiac tissue. In some embodiments, the processor assesses the qualities of physical contact by identifying a distinct frequency response of tissue to the AC signal (for example, in contrast to the frequency response of blood) for each distal electrode separately.

In an embodiment, the oscillator circuit modulates the intra-cardiac signals in two or more AC frequencies simultaneously. In another embodiment, the AC frequency of the oscillator circuit is varied (e.g., by commands from the processor) over a range of frequencies that are most indicative of the type of tissue. In an embodiment, the oscillator circuit is configured vary the AC signal over time between the two or more AC frequencies. In either case, the processor analyzes the resulting frequency-dependent signals at the two or more AC frequencies, and accordingly provides an assessment whether the distal electrode is in direct electrical contact with (i.e., touches) cardiac tissue or not (e.g., electrode is immersed in blood). As noted above, the indication is provided independently for each distal electrode.

A technique for sensing of electrode-tissue physical contact using analysis of frequency response of tissue is described in U.S. patent application Ser. No. 15/991,291, filed May 29, 2018, entitled "Touch Detection by Different Frequency Response of Tissue," which is assigned to the assignee of the present patent application and whose disclosure is incorporated herein by reference. In an embodiment, the processor may use this method for analyzing the acquired intra-cardiac signals.

The disclosed technique for estimation of electrode-tissue contact by applying AC signal to a common ground simplifies the technology and procedures required for a reliable acquisition of intra-cardiac electrophysiological signals, such as intra-cardiac ECG signals. Thus, the disclosed technique may simplify invasive diagnostic and therapeutic procedures using a catheter-based system, such as for diagnosing and treating arterial fibrillation.

System Description

FIG. 1 is a schematic, pictorial illustration of an electro-anatomical mapping system 21, in accordance with an embodiment of the present invention. In some embodiments, system 21 is used for multi-channel measurement of AC modulated intra-cardiac ECG signals.

FIG. 1 depicts a physician 27 using an electro-anatomical catheter 29 to perform an electro-anatomical mapping of a heart 23 of a patient 25. Catheter 29 comprises, at its distal end, one or more arms 20, which may be mechanically flexible, to each of which are coupled one or more distal electrodes 22.

During the electro-anatomical mapping procedure, a tracking system is used to track the intra-cardiac locations of distal electrodes 22, so that each of the acquired electrophysiological signals may be associated with a known intra-cardiac location. An example of tracking system is Active Current Location (ACL), which is described in U.S. Pat. No. 8,456,182, whose disclosure is incorporated herein by reference. In the ACL system, a processor estimates the respective locations of the distal electrodes based on impedances measured between each of distal electrodes 22 and a plurality of surface electrodes 24 that are coupled to the skin of patient 25 (For ease of illustration, only one surface-electrode is shown in FIG. 1). The processor may then associate any electrophysiological signal received from distal electrodes 22 with the location at which the signal was acquired.

In some embodiments, multiple distal electrodes 22 acquire intra-cardiac ECG signals from tissue of a cardiac chamber of heart 23. A signal acquisition circuitry 44 is coupled to receive the intra-cardiac signals via an electrical interface 35. An oscillator (shown in FIG. 2 below) modulates the intra-cardiac signals with an AC signal, as will be described in detail below. Signal acquisition circuitry 44 digitizes the AC modulated intra-cardiac signals so as to produce multiple digital signals. Then, signal acquisition circuitry 44 conveys the digitized signals to processing unit 42, included in processor 28, which detects the AC signal in the multiple digital signals. Based on the detected AC signal, processing unit 42 assesses respective qualities of physical contact between each of distal electrodes 22 and cardiac tissue.

In some embodiments, signal acquisition circuitry 44, as well as processing unit 42, are part of processor 28 and therefore the use of the term "processor 28" for describing the embodiments of circuitry 44 and unit 42 should be considered as equivalent to using the terms "Signal acquisition circuitry 44" and/or "processing unit 42."

In some embodiments, the assessment of qualities of physical contact is based, for example, on modeling the frequency response of the impedances sensed by each of electrodes 22, which is different for blood and tissue, as elaborated in the above described U.S. patent application Ser. No. 15/991,291, and as described below. The structure and operation of signal acquisition circuitry 44 is described in more detail below with respect to FIG. 2.

In some embodiments, processing unit 42 uses information contained in the ECG signals, for example, to construct an electro-anatomical map 31. In some embodiments, processor 28 uploads from a memory 36 modulated intra-cardiac ECG signals that were measured at a previous probing session, in order to assess the quality of physical contact during that session.

In some embodiments, multiple distal electrodes 22 acquire intra-cardiac ECG signals from tissue of a cardiac chamber of heart 23. A signal acquisition circuitry 36 is coupled to receive the intra-cardiac signals via an electrical interface 35. An oscillator (shown in FIG. 2 below) modulates the intra-cardiac signals with an AC signal, as will be described in detail below. Signal acquisition circuitry 36 digitizes the AC modulated intra-cardiac signals so as to produce multiple digital signals. Then, signal acquisition circuitry 36 conveys the digitized signals to processing unit 42, included in processor 28, which detects the AC signal in the multiple digital signals. Based on the detected AC signal, unit 42 assesses In some embodiments, processing unit 42 is further configured to analyze the intra-cardiac ECG signals and may present the results of the analysis in a standard ECG format, typically a graphical representation moving with time, on display 26.

The example illustration shown in FIG. 1 is chosen purely for the sake of conceptual clarity. For example, position measurements can also be done by applying a voltage gradient between pairs of surface electrodes 24 and measuring, with distal electrodes 22, the resulting potentials (i.e., using the Carot®4 technology produced by Biosense-Webster, Irvine, Calif.). Thus, embodiments of the present invention apply to any position sensing method that uses distal electrodes to apply and/or measure modulated electrical signals.

Other types of catheters, such as the Lasso® Catheter (produced by Biosense-Webster), or a basket catheter, may equivalently be employed. Contact sensors may be fitted at the distal end of electro-anatomical catheter 29. Other types of electrodes, such as those used for ablation, may be utilized in a similar way on distal electrodes 22 to acquire intra-cardiac electrophysiological signals that are modulated by one or more AC frequencies. Thus, an ablation electrode used for collecting frequency-dependent electrophysiological data is regarded in this description as a distal electrode.

Processor 28 and processing unit 42 typically comprise general-purpose processors with software programmed to carry out the functions described herein. The software may be downloaded to either processor in electronic form, over a network, for example, or it may, alternatively or additionally, be provided and/or stored on non-transitory tangible media, such as magnetic, optical, or electronic memory.

Figure 2:
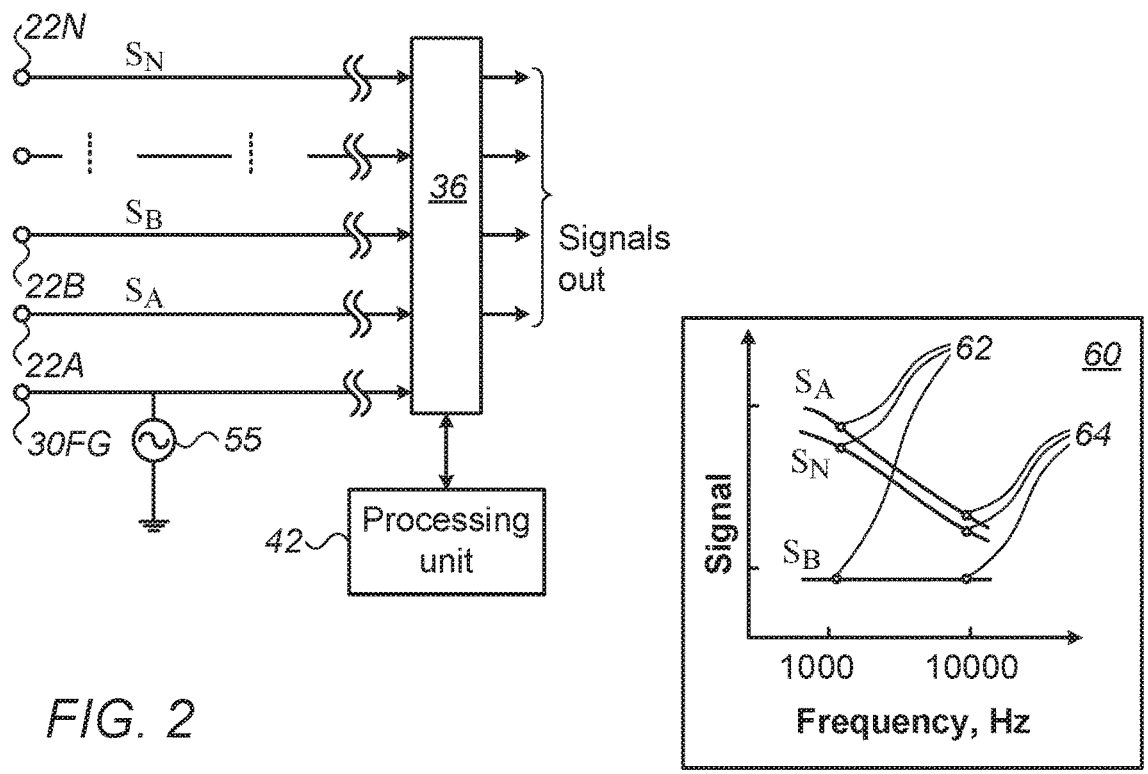
FIG. 2 is a schematic block diagram of signal acquisition circuitry and an oscillator circuit, in accordance with an embodiment of the present invention.

Estimation of Electrode-Tissue Contact Using Oscillator at Common Ground of ECG System FIG. 2 is a schematic block diagram of signal acquisition circuitry 44 and an oscillator circuit 55, in accordance with an embodiment of the present invention. As seen, surface contact 30FG, which is coupled to the body of the patient, serves, among other possible functions, as a common ground signal and as an output lead of an oscillator circuit 55. Contact 30FG may be a surface electrode attached to the body, or a contact point between one or more surface electrodes that are in contact with the skin or an internal organ of the body, for example surface-skin ECG recording electrodes.

In some embodiments, oscillator circuit 55 AC modulates the electric potential of floating ground 30FG, thereby modulating intra-cardiac ECG signals $S_A$, $S_B$, $S_N$.

Any suitable AC signal can be used. In an embodiment, the AC signal generated by oscillator circuit 55 has two or more AC frequencies. AC Modulated intra-cardiac ECG signals $S_A$, $S_B$, $S_N$, are acquired by multiple distal electrodes 22A, 22B, . . . 22N, respectively. In another embodiment, oscillator circuit 55 variably modulates ECG signals $S_A$, $S_B$, $S_N$ (i.e., as with AC frequency that is time-dependent), so as to generate the AC frequency dependent intra-cardiac ECG signals $S_A$, $S_B$, $S_N$. As noted above, the modulated intra-cardiac ECG signals $S_A$, $S_B$, $S_N$, propagate through blood or tissue and in the process are received at signal acquisition circuitry 44.

In some embodiments, an Analog-to-Digital Converter (ADC) inside signal acquisition circuitry 44 (not shown) digitizes signals $S_A$, $S_B$, $S_N$. In an embodiment, the ADC is configured to simultaneously digitize at least one of the intra-cardiac signals and the corresponding AC signal.

The ADC outputs the digitized signals to processing unit 42 that detects the AC signal in the multiple digital signals $S_A$, $S_B$, . . . $S_N$, and assess, based on the detected AC signal, respective qualities of physical contact between the electrodes and cardiac tissue (e.g., by detecting, per intra-cardiac signal, whether the detected AC signal matches a frequency response of blood or of cardiac tissue).

For example, for any given distal electrode 22K (K=A, B, . . . N) among electrodes 22A, 22B, . . . 22N, processing unit 42 assesses the stability of the physical contact of the electrode with tissue while acquiring the intra-cardiac ECG signal, as described below.

In some embodiments, the technique for contact sensing using analysis of frequency response of tissue, as described in U.S. patent application Ser. No. 15/991,291, is applied. As shown in inset 60, by way of example, the values of AC modulated intra-cardiac ECG signals $S_A$ and $S_N$ of electrodes 22A and 22N are highly frequency dependent, wherein the x-axis in inset 60 represents AC frequency. As seen in inset 60, unit 42 finds, for example, distinct positive difference between signals 62 and signals 64 for $S_A$ and $S_N$). Based on the differences between signals $S_A$ and $S_N$, processing unit 42 assesses that electrodes 22A and 22N are in firm (e.g., stable) physical contact with tissue. Intra-cardiac ECG signals $S_B$, on the other hand, are practically AC frequency independent (i.e., the differences between signals 62 and signals 64 are approximately zero for $S_B$), which causes unit 42 to assess, for example, that electrode 22B is immersed in blood, or, as another example, frequently loses contact with tissue (i.e., electrode is in an unstable physical contact with tissue).

The example illustration shown in FIG. 2 is chosen purely for the sake of conceptual clarity. FIG. 2 shows only parts relevant to embodiments of the present invention. Other system elements, such as external ECG recording electrodes and their connections are omitted. Various ECG recording system elements are omitted, as well such as elements for filtering, digitizing, protecting circuitry, and others. In an optional embodiment, oscillator circuit 55 is included in a read-out application-specific integrated circuit (ASIC) that is used for measuring intra-cardiac AC modulated ECG signals $S_A$, $S_B$, . . . $S_N$.

The various elements for routing signal acquisition circuitry 44 may be implemented in hardware, e.g., using one or more discrete components, such as field-programmable gate arrays (FPGAs) or ASICs. In some embodiments, some elements of signal acquisition circuitry 36 and/or processing unit 42 may be implemented in software, or by using a combination of software and hardware elements.

Other methods may be applied that use modulated signals ECG signals $S_A, S_B, \ldots S_N$, to assess quality of physical contact. For example, in an optional embodiment, statistical analysis of set pair signals $(S_J, S_K)$, (J, K=A, B, . . . N) may indicate which of electrodes 22A, 22B, . . . 22N are in physical contact with tissue, and which are in blood.

Figure 3:
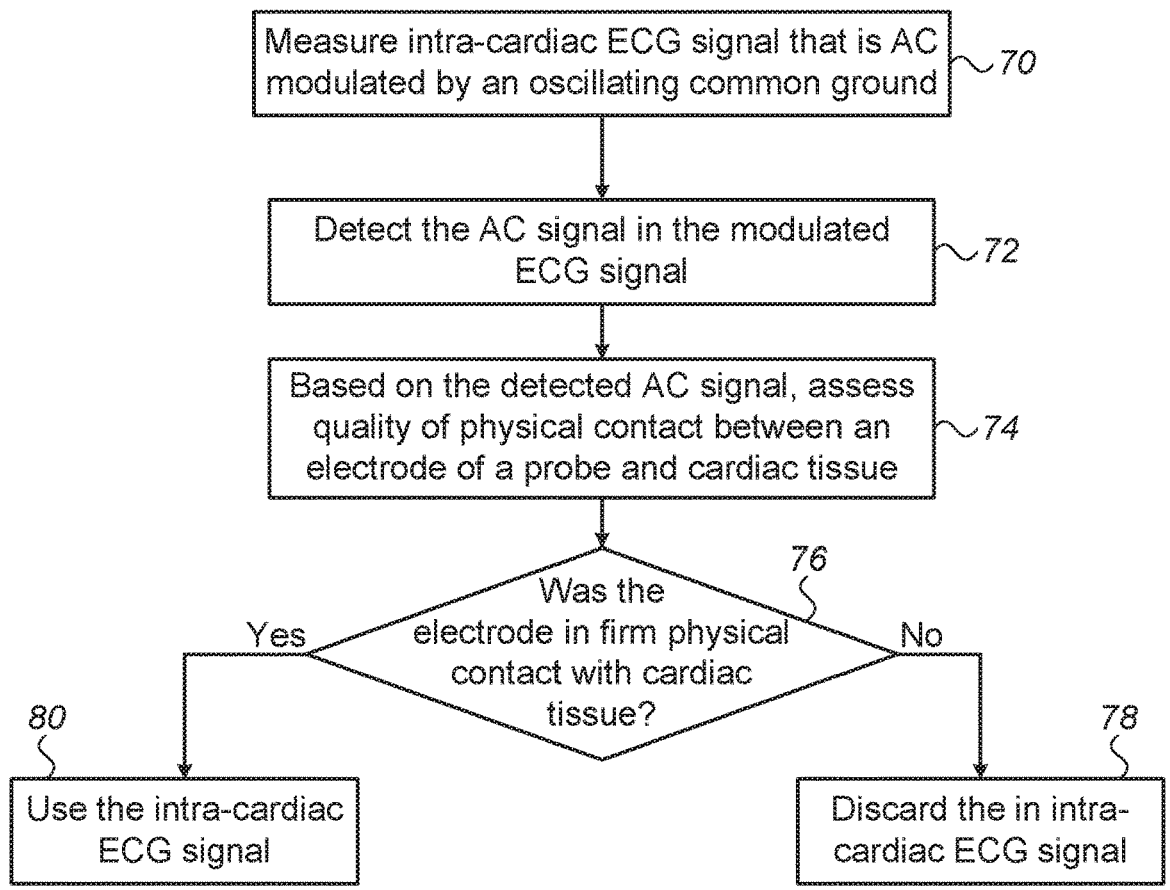
FIG. 3 is a flow chart that schematically illustrates a method for assessing the quality of physical contact between an electrode and cardiac tissue using AC signal, in accordance with an embodiment of the present invention.

FIG. 3 is a flow chart that schematically illustrates a method for assessing the quality of physical contact between an electrode and cardiac tissue using AC signal, in accordance with an embodiment of the present invention. The process begins with system 21 measuring AC modulated intra-cardiac ECG signals $S_A, S_B, \ldots S_N$, using multiple distal electrodes 22A, 22B, . . . 22N, at an intra-cardiac signals measurement step 70.

At an AC signal detection step 72, processing unit 42 detects the AC signal in multiple digital signals $S_A, S_B, \ldots S_N$.

In a quality of contact assessment step 74, based on the detected AC signal processor 28 assesses, for each of the respective electrodes 22A, 22B, . . . 22N, the electrode acquired the ECG signal while being in firm physical contact with tissue, as described above.

If, at a decision step 76, processor 28 assesses that a given distal electrode is not in physical contact with tissue, processor 28 discards the respective intra-cardiac ECG signals (e.g., ignores it), at a dropping step 78. If processor 28 assesses that a given distal electrode is in physical contact with tissue, then processor 28 uses the acquired intra-cardiac ECG signals, at an ECG signals usage step 80, for example by unit 42 processing it to include information embedded in the ECG signal in an electro-anatomical map 31.

The procedure may be iterated (i.e., return to step 70) at a same location over cardiac tissue, or, after a repositioning of catheter 29, performed at another location on the inner surface of a cardiac chamber of heart 23.

The example flow chart shown in FIG. 3 is chosen purely for the sake of conceptual clarity. In alternative embodiments, various additional methods and/or sensors may be applied in parallel to assess physical contact of one or more electrodes 22 with tissue, for example, based on their locations as measured by the ACL method described above.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
   signal acquisition circuitry, which is configured to receive from an intra-cardiac probe multiple intra-cardiac signals acquired by multiple electrodes of the probe, and to further receive a common ground signal for the multiple intra-cardiac signals, and to digitize the intra-cardiac signals relative to the common ground signal so as to produce multiple digital signals;
   an oscillator circuit, which is configured to generate an Alternating Current (AC) signal and to apply the AC signal to the common ground signal provided to the signal acquisition circuitry thereby modulating the multiple intracardiac signals; and
   a processor, configured to detect the AC signal in the modulated multiple digital signals, and to assess, based on the detected AC signal, respective qualities of physical contact between the electrodes and cardiac tissue by identifying distinct frequency response of tissue to the AC signal for each of the multiple electrodes separately.

2. The system according to claim 1, wherein the oscillator circuit is configured to generate and apply the AC signal at two or more AC frequencies.

3. The system according to claim 2, wherein the oscillator circuit is configured to generate and apply the two or more AC frequencies simultaneously.

4. The system according to claim 2, wherein the oscillator circuit is configured to vary the AC signal over time between the two or more AC frequencies.

5. The system according to claim 2, wherein the processor is configured to assess the qualities of physical contact by detecting, per intra-cardiac signal, whether the detected AC signal matches a frequency response of blood or of cardiac tissue.

6. The system according to claim 1, wherein the processor is configured to assess the respective qualities of physical contact based on one or more AC signals uploaded from a memory.

7. The system according to claim 1, wherein the processor is configured to assess the respective qualities of physical contact in real-time.

8. The system according to claim 1, wherein the acquisition circuitry comprises at least one Analog-to-Digital Converter (ADC), which is configured to simultaneously digitize at least one of the intra-cardiac signals and the corresponding AC signal.

9. A method, comprising:
   receiving from an intra-cardiac probe multiple intra-cardiac signals acquired by multiple electrodes of the probe, further receiving a common ground signal for the multiple intra-cardiac signals, and digitizing the intra-cardiac signals relative to the common ground signal so as to produce multiple digital signals;
   generating an Alternating Current (AC) signal and applying the AC signal to the common ground signal provided to the signal acquisition circuitry thereby modulating the multiple intracardiac signals; and
   detecting the AC signal in the modulated multiple digital signals, and assessing, based on the detected AC signal, respective qualities of physical contact between the electrodes and cardiac tissue by identifying distinct frequency response of tissue to the AC signal for each of the multiple electrodes separately.

10. The method according to claim 9, wherein generating and applying the AC signal comprises generating and applying the AC signal at two or more AC frequencies.

11. The method according to claim 10, wherein generating and applying the AC signal comprises generating and applying the AC signal at the two or more AC frequencies simultaneously.

12. The method according to claim 10, wherein generating and applying the AC signal comprises varying the AC signal over time between the two or more AC frequencies.

13. The method according to claim 10, wherein assessing the qualities of physical contact comprises assessing the qualities of physical contact by detecting, per intra-cardiac signal, whether the detected AC signal matches a frequency response of blood or of cardiac tissue.

14. The method according to claim 9, wherein assessing the qualities of physical contact comprises assessing the qualities of physical contact based on one or more AC signals uploaded from a memory.

15. The method according to claim 9, wherein assessing the qualities of physical contact comprises assessing the qualities of physical contact in real-time.

16. The method according to claim 9, wherein digitizing the intra-cardiac signals relative to the common ground signal comprises simultaneously digitizing at least one of the intra-cardiac signals and the corresponding AC signal using an Analog-to-Digital Converter (ADC).

* * * * *